(12) United States Patent
Lin et al.

(10) Patent No.: US 8,308,705 B2
(45) Date of Patent: Nov. 13, 2012

(54) APPARATUS FOR FLUID COLLECTION

(75) Inventors: Zhan-Sheng Lin, Taipei County (TW);
Nan-Kuang Yao, Taoyuan County (TW)

(73) Assignee: Industrial Technology Research Institute, Hsinchu (TW)

( * ) Notice: Subject to any disclaimer, the term of this patent is extended or adjusted under 35 U.S.C. 154(b) by 555 days.

(21) Appl. No.: 12/488,805

(22) Filed: Jun. 22, 2009

(65) Prior Publication Data

US 2010/0160881 A1 Jun. 24, 2010

(30) Foreign Application Priority Data

Dec. 19, 2008 (TW) ................................ 97149680 A

(51) Int. Cl.
*A61M 1/00* (2006.01)
*A61F 13/00* (2006.01)

(52) U.S. Cl. ........ 604/327; 604/304; 604/305; 604/307; 604/308; 604/315; 604/318; 602/47; 602/56; 602/900

(58) Field of Classification Search .................. 604/327, 604/307, 308, 318, 315, 304, 305; 602/47, 602/56, 900
See application file for complete search history.

(56) References Cited

U.S. PATENT DOCUMENTS

| | | | |
|---|---|---|---|
| 1,178,644 A | 4/1916 | Johnson | |
| 4,124,116 A * | 11/1978 | McCabe, Jr. | 96/108 |
| 4,541,426 A * | 9/1985 | Webster | 602/47 |
| 4,573,986 A | 3/1986 | Minetola et al. | |
| 4,747,960 A * | 5/1988 | Freeman et al. | 210/689 |
| 5,107,859 A * | 4/1992 | Alcorn et al. | 128/853 |
| 5,328,450 A * | 7/1994 | Smith et al. | 602/59 |
| 5,531,999 A * | 7/1996 | Cartmell et al. | 424/445 |
| 5,549,587 A * | 8/1996 | Norton | 604/333 |
| 5,554,659 A * | 9/1996 | Rosenblatt | 521/51 |
| 5,695,489 A | 12/1997 | Japuntich | |
| 5,830,170 A * | 11/1998 | Whiteman et al. | 604/1 |
| 5,845,641 A * | 12/1998 | Pinney et al. | 128/849 |
| 5,885,237 A * | 3/1999 | Kadash et al. | 602/48 |
| 5,902,260 A * | 5/1999 | Gilman et al. | 602/57 |
| 5,970,979 A * | 10/1999 | Christofel et al. | 128/849 |
| 6,143,945 A * | 11/2000 | Augustine et al. | 602/41 |
| 6,569,133 B2 * | 5/2003 | Cheng et al. | 604/329 |
| 6,974,428 B2 * | 12/2005 | Knutson et al. | 602/2 |
| 7,018,366 B2 | 3/2006 | Easter | |
| 7,066,918 B2 | 6/2006 | Charles | |
| 7,220,250 B2 | 5/2007 | Suzuki et al. | |
| 7,771,377 B2 * | 8/2010 | Stapf et al. | 602/3 |

(Continued)

FOREIGN PATENT DOCUMENTS

CH 556272 11/1974

(Continued)

OTHER PUBLICATIONS

German Patent Office Action issued on Feb. 1, 2012.

(Continued)

*Primary Examiner* — Kevin C Sirmons
*Assistant Examiner* — Ginger T Chapman
(74) *Attorney, Agent, or Firm* — WPAT PC; Justin King

(57) ABSTRACT

An apparatus for fluid collection is disclosed, which comprises: a frame, composed of a plurality of unit cells, each being made of an absorbent polymer composite; and a bag, for receiving the frame while being connected to a conduit provided for enabling a fluid to flow in and out the bag therethrough.

22 Claims, 10 Drawing Sheets

U.S. PATENT DOCUMENTS

| | | | |
|---|---|---|---|
| 7,815,616 B2 * | 10/2010 | Boehringer et al. | 604/313 |
| 7,863,495 B2 * | 1/2011 | Aali | 602/42 |
| 7,896,864 B2 * | 3/2011 | Lockwood et al. | 604/541 |
| 7,928,281 B2 * | 4/2011 | Augustine | 602/48 |
| 2001/0037097 A1 | 11/2001 | Cheng et al. | |
| 2003/0004473 A1 * | 1/2003 | Bonadio et al. | 604/315 |
| 2003/0073964 A1 * | 4/2003 | Palumbo et al. | 604/332 |
| 2003/0088201 A1 * | 5/2003 | Darcey | 602/44 |
| 2003/0120194 A1 * | 6/2003 | Stapf | 602/48 |
| 2004/0176731 A1 | 9/2004 | Cheng et al. | |
| 2006/0235347 A1 * | 10/2006 | Aali | 602/41 |
| 2007/0055209 A1 * | 3/2007 | Patel et al. | 604/315 |
| 2008/0312572 A1 * | 12/2008 | Riesinger | 602/43 |
| 2010/0262090 A1 * | 10/2010 | Riesinger | 604/304 |

FOREIGN PATENT DOCUMENTS

| | | |
|---|---|---|
| EP | 1470807 A | 10/2004 |
| JP | 2001190581 A | 7/2001 |

OTHER PUBLICATIONS

GB patent search report issued on Oct. 23, 2009.
FR patent search report issued on Oct. 29, 2010.

* cited by examiner

APPARATUS FOR FLUID COLLECTION

FIELD OF THE INVENTION

The present invention relates to an apparatus for fluid collection, and more particularly, to a flexible, non-directional fluid collecting apparatus with display module for display amount of fluid being accumulated therein that can be worn next to the skin on any position of user's body as it is build with sufficient strength for resisting compression.

BACKGROUND OF THE INVENTION

Since most medical fluid collection bags, such as urine collection bags, surgical drainage bags and wound fluid collection bags for negative pressure wound therapy (NPWT), etc., are supposed to be used for several days or even several months, in addition to the basic demand of leakage proof, smell-less and large storage capability, it is preferred to have such medical fluid collection bags that can be worn or attached comfortably to human body in a concealed manner for enabling the patient wearing such bags to walk or exercise without too much trouble.

An unused medical fluid collection bag or a new medical fluid collection bag that is just being attached to a patient for fluid collection is like a flat balloon, so that it is usually being tied and worn on a patient's body without slipping off by bandage or elastic clothing. However, as the weight and the volume of such medical fluid collection bag will increase significantly after being worn by the patient for a period of time, how to wear such medical fluid collection bag properly and comfortable on the patient's body is becoming a dilemma. That is, if a new medical fluid collection bag is loosely tied on the patient's body, the weight of the fluid being collected in such bag will certainly cause the same to wobble or even move; but if the new medical fluid collection bag is tightly tie on the patient's body, the pressure from the bandage for tying the bag is going to increase with the expansion of the bag which is certainly going to cause discomfort to the patient, or even becoming the cause of resisting for blocking fluid from flowing into the bag.

For those medical fluid collection bags used in negative pressure wound therapy (NPWT) or vacuum assisted closure (V.A.C.) therapy, they are structured for receiving cellular waste and excess tissue fluid from a wound that was withdrawn by a negative pressure formed inside the wound as the aforesaid adjuvant physical therapy applies a suction pump to a patch of a bio-compatible porous wound dressing covering the wound. Similarly, such medical fluid collection bag adapted for NPWT or VAC should be configured in such a way that it can be worn on a patient's body comfortably for a conceivable period of time without compromising in any way regarding to the patient's daily operations. However, as such fluid collection bag adapted for NPWT or VAC should be connected to the suction pump, it is required to be made of a material of a specific hardness that, instead of a bag, it is more like a bulky, heavy, directional tank that not only it is can be tilted easily and thus causing the collected wound fluid to back flow, but also it is not convenient for carriage and not pleasing to the eye.

There are already some studies trying to improve such medical fluid collection bag. One of which is disclosed in U.S. Pat. No. 7,018,366, entitled "Vacuum assisted relief system (VARS)", which includes: a garment, capable of being worn like a diaper or underwear and having an intake manifold comprised of a number of perforated tubes sandwiched between layers of material; an electric pump; and a receiver with electric scale for display amount of fluid being collected. When the garment is worn on a user, urine from the user may be collected in the garment and drawn into the manifold tubes and finally to the receiver by means of vacuum from the pump. Although the aforesaid VARS can be worn easily and comfortable on a user like a diaper or underwear, its receiver is restricted to be mounted and located at a comparative lower position relative to the user's body, such as the user's leg, as the receiver is a directional bag that is detachable arranged. However, such configuration is going to hamper the user's movement since the weight and the volume of the receiver is going to increase several times to hundred times after being used for a period of time.

Another such study is a liquid waste collection chamber assembly disclosed in U.S. Pat. No. 7,066,918, entitled "Closed coupled urine collection chamber". The aforesaid liquid waste collection chamber assembly is a flat urine bag provided for liquid waste from the user to flow therein in response to gravitational force. The aforesaid device is advantageous in its small size that it can be adhere to the surface of urethral meatus for urine collection. However, it is disadvantageous in that: it is incapable of allowing a user to aware the amount of urine that had been collected, and it is not comfortable to wear as it is made of hard material.

One another study is a urine receiver disclosed in U.S. Pat. No. 7,220,250, entitled "Urine receiver and urine collection processing system implementing urine receiver". The urine collection processing system is able to detect urine or humidity automatically by an electric means and is designed to feed the collected urine to the urine receiver. Nevertheless, it is disadvantageous in that: it is heavy and requires an external power supply, and the urine receiver is not designed for carriage and also not capable of being attached to or worn on limbs/torso of a user.

SUMMARY OF THE INVENTION

The present invention relates to a flexible, non-directional fluid collecting apparatus with display module for display amount of fluid being accumulated therein that can be worn next to the skin on any position of user's body as it is build with sufficient strength for resisting compression.

To achieve the above object, the present invention provides an apparatus for fluid collection, comprising: a frame, composed of a plurality of unit cells, each being made of an absorbent polymer composite; and a bag, for receiving the frame while being connected to a conduit provided for enabling a fluid to flow in and out the bag therethrough.

Further scope of applicability of the present application will become more apparent from the detailed description given hereinafter. However, it should be understood that the detailed description and specific examples, while indicating exemplary embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given herein below and the accompanying drawings which are given by way of illustration only, and thus are not limitative of the present invention and wherein.

DESCRIPTION OF THE EXEMPLARY EMBODIMENTS

For your esteemed members of reviewing committee to further understand and recognize the fulfilled functions and structural characteristics of the invention, several exemplary embodiments cooperating with detailed description are presented as the follows.

Figure 1:
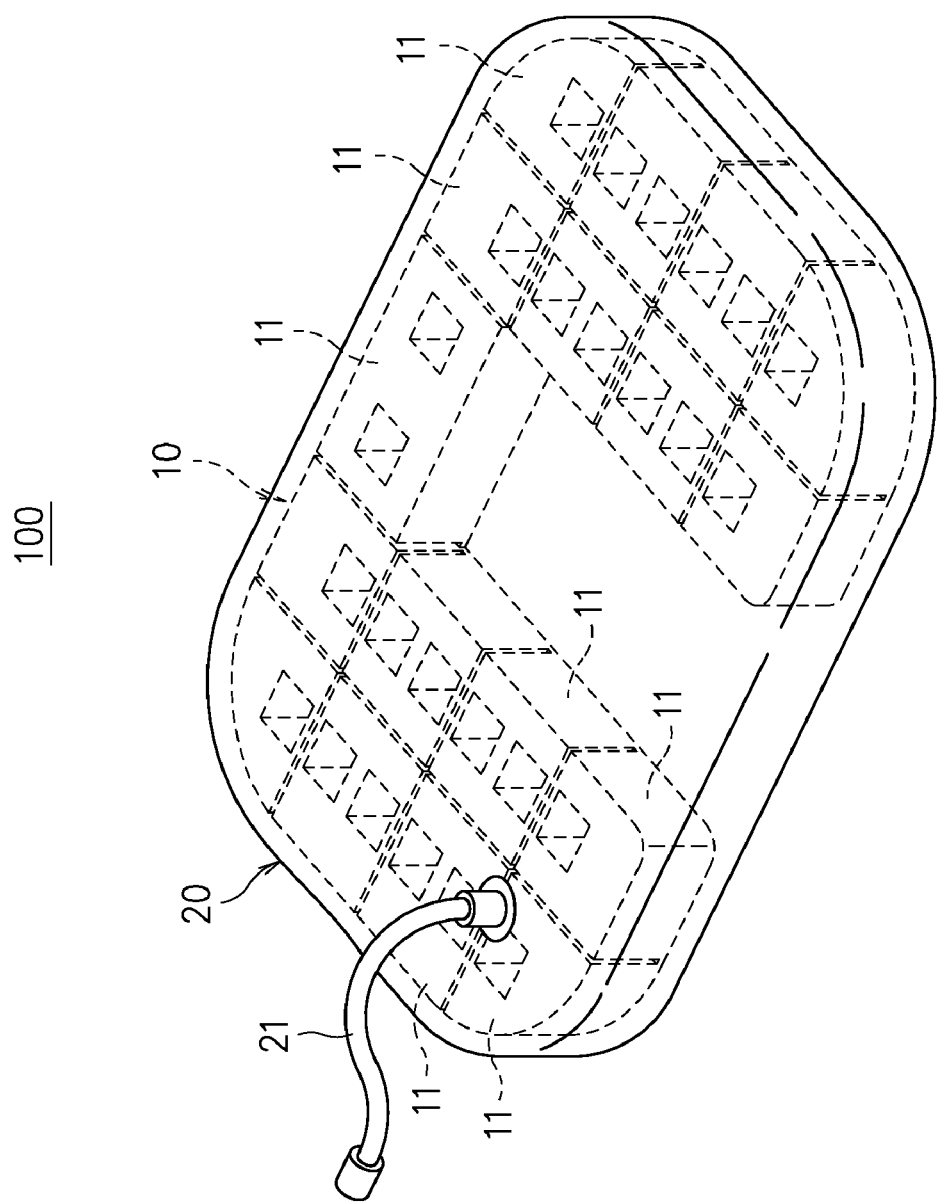
FIG. 1 is a three-dimensional view of an apparatus for fluid collection according to an embodiment of the invention.

Please refer to FIG. 1, which is a three-dimensional view of an apparatus for fluid collection according to an embodiment of the invention. The fluid collection apparatus 100 of FIG. 1 is designed for collecting fluids such as urine or excess tissue fluid from a wound, which comprises: a frame 10 and a bag 20. The frame 10 is composed of a plurality of unit cells 11 that are made of an absorbent polymer composite such as polyvinyl alcohol (PVA). It is noted that not only PVA has good water absorbency, but also the dry PVA, being a hard solid material, can be softened after soaking without significant volume expansion. The bag 20 is used for receiving the frame 10 that is connected to a conduit 21 provided for the fluid such as urine or tissue fluid to flow in and out the bag 20 therethrough. The bag 20 is made of a flexible material with a specific degree of transparency, such as polyvinyl chloride (PVC) film.

Figure 2:
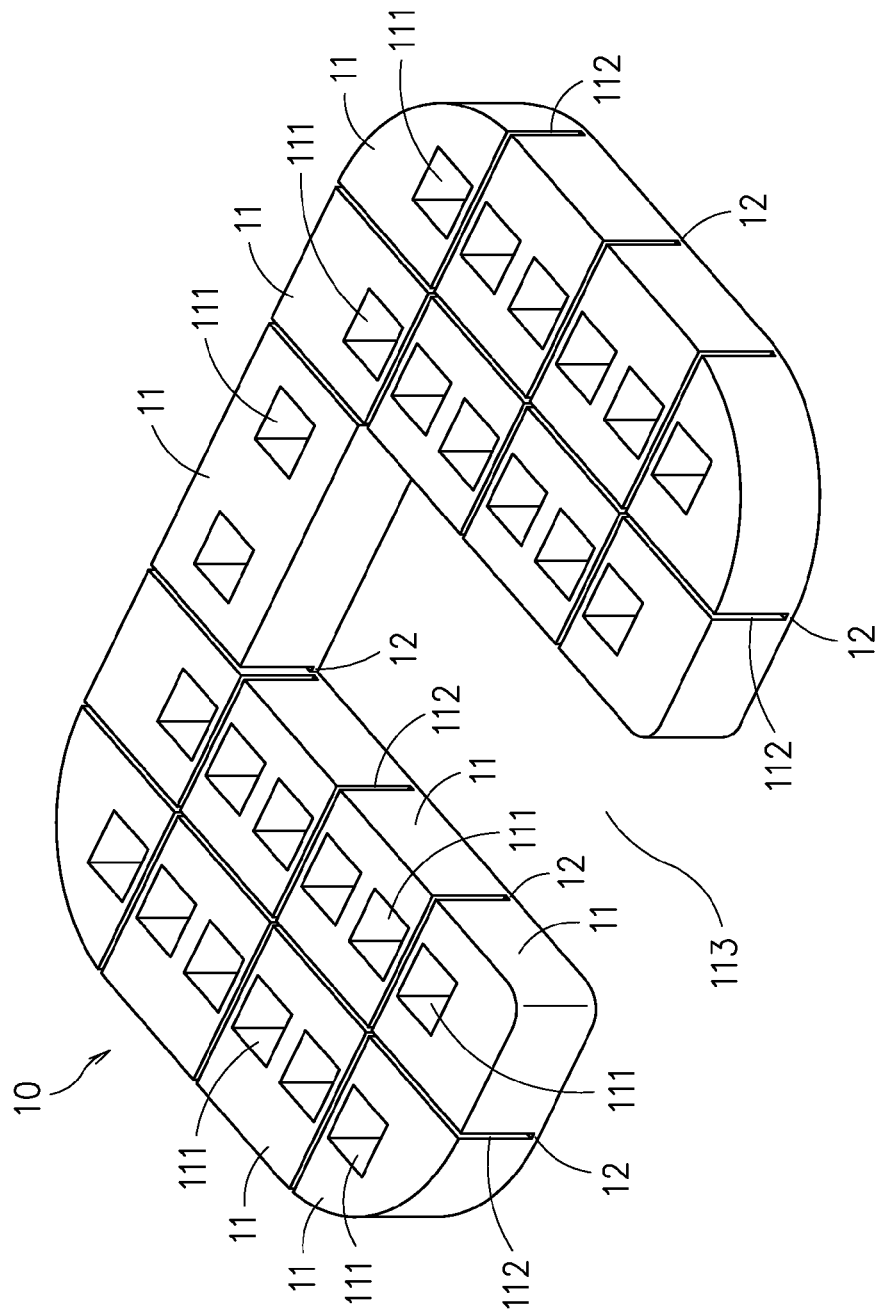
FIG. 2 is a three-dimensional view of a frame used in an embodiment of the invention.
Figure 3:
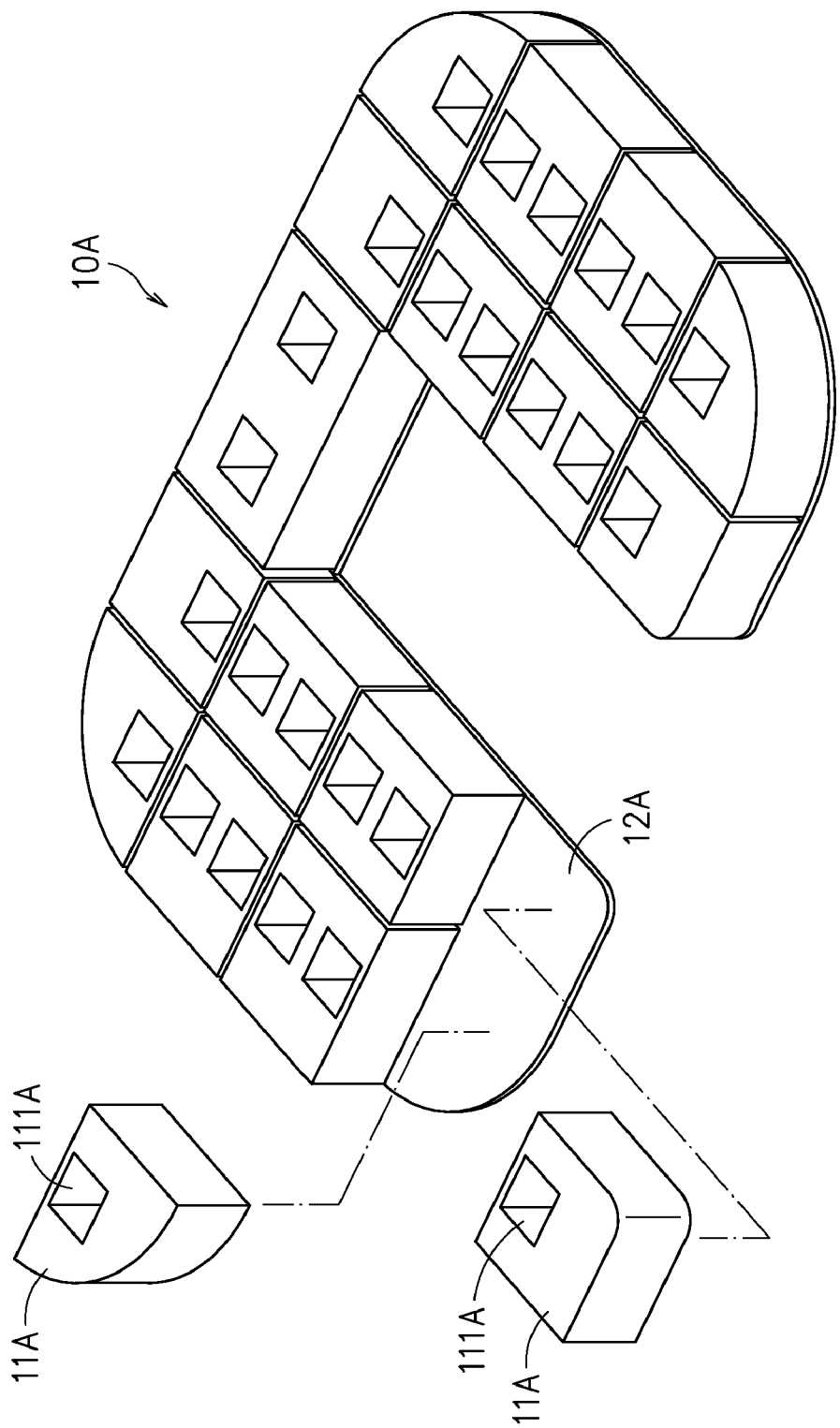
FIG. 3 is a schematic diagram showing how unit cells are connected by the use of a connector for forming a frame used in an embodiment of the invention.
Figure 13:
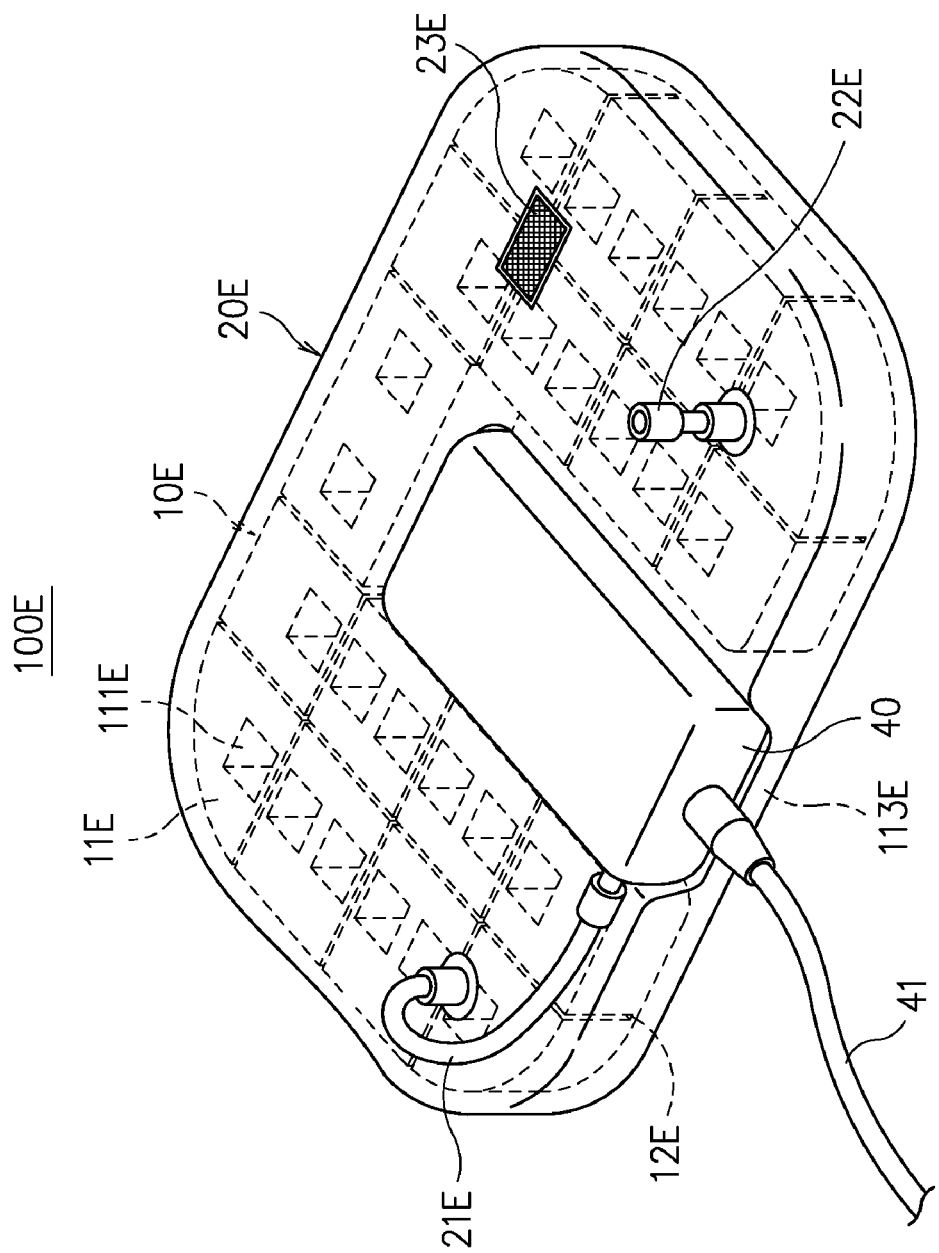
FIG. 13 is a three-dimensional view of an apparatus for fluid collection according to another embodiment of the invention.

Please refer to FIG. 2, which is a three-dimensional view of a frame used in an embodiment of the invention. In FIG. 2, the plural unit cells 11 are coplanar-disposed on a configuration plane as an inverted U-shaped array with an indentation 113, in that the indentation 113 is designed for a pump 40 to fit therein, as shown in FIG. 13. It is noted that the plural unit cells 11 can be arranged into array of any shape without being limited by the aforesaid embodiment. In this embodiment, the plural unit cells 11 are formed with the same thickness but into different shapes. Nevertheless, each unit cell 11 is formed with at a penetrating hole 111, which is arranged penetrating the corresponding unit cell 11 in a directing perpendicular to the configuration plane of the plural unit cells 11. Thereby, there is a plurality of such holes 111 formed in the frame 10 that are arranged as an array. In addition, the plural unit cells 11 are connected with each other by the use of at least one connector 12. The at least one connector 12 is disposed on the same configuration plane for enabling the sides of the plural unit cells 11 corresponding to the at least one connector 12 to be interconnected with each while leaving the other sides thereof opposite to the at least one connector 12 to be disconnected. There are many varieties regarding to how the unit cells 11 and connectors 12 are formed and shaped. In this embodiment, the frame 10 are manufactured by forming a plurality of non-penetrating grooves 112 on a block of raw material and consequently allowing the bottoms of any two neighboring unit cells 11 to be interconnected, by that the connectors 12 and the plural unit cells 11 are integrally formed. In another embodiment shown in FIG. 3, as there is a plurality of unit cells 11A, that are formed of different shapes and each has at least one holes 111A, being formed independently, the frame 10A can be formed by attaching the plural unit cells 11A on an adhesive film or adhesive tape in an one-by-one manner whereas the adhesive film or tape is acting as the connectors 12A for connecting the plural unit cells 11A.

Figure 6:
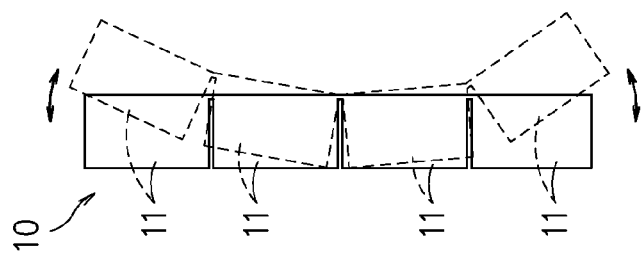
FIG. 6 is a right-side view of FIG. 4 as it is being bended.
Figure 4:
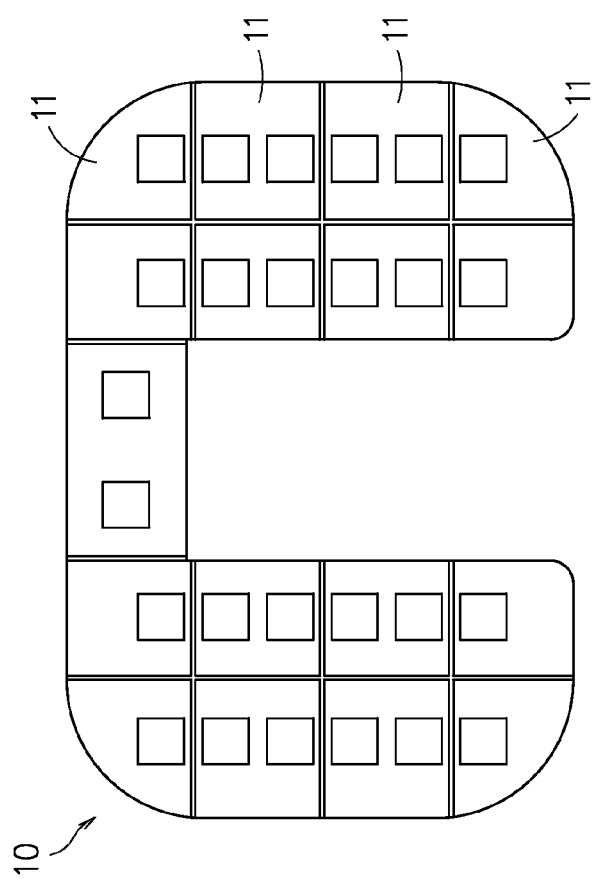
FIG. 4 is a front view of a frame used in an embodiment of the invention.
Figure 5:
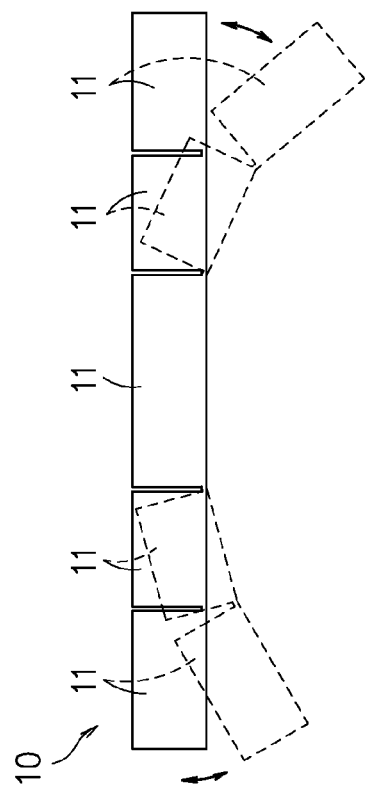
FIG. 5 is a bottom view of FIG. 4 as it is being bended.

Please refer to FIG. 4 to FIG. 6, which show a frame 10 used in an embodiment of the invention as it is being bended. As any two neighboring unit cells 11 in the frame 10 are connected by one side thereof while detaching at another, the frame 10 can be bended at will according to actual requirement while allowing different unit cells 11 to be bended with different bending angles. The bottom view of FIG. 5 and the right-side view of FIG. 6 show that the frame 10 can be bended with respect to two perpendicular axial directions, so that it is possible to bend the frame 10 with respect to the two perpendicular axial directions simultaneously for adapting the same to fit on a curved surface, such as a hips, a head, a limb or a torso, etc. Since the bag 20 that is designed to be received inside the frame 10 is made of a water-proof flexible material, the bag 20 can be bended along the bending of the frame 10.

Figure 7:
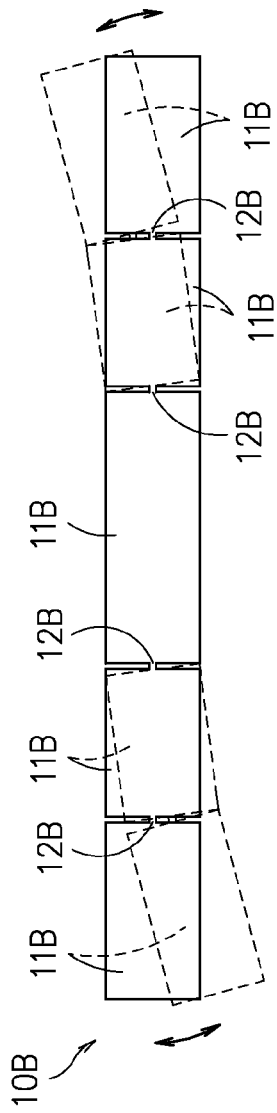
FIG. 7, FIG. 8 and FIG. 9 are bottom views of various frames according to different embodiment of the invention as they are being bended.
Figure 8:
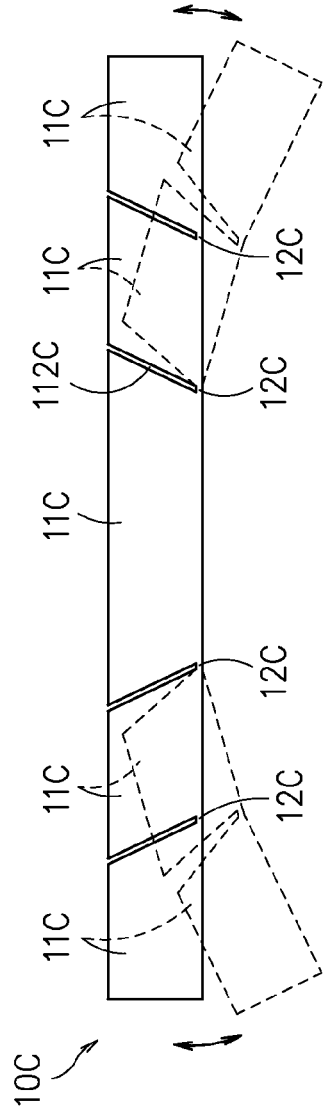
Figure 9:
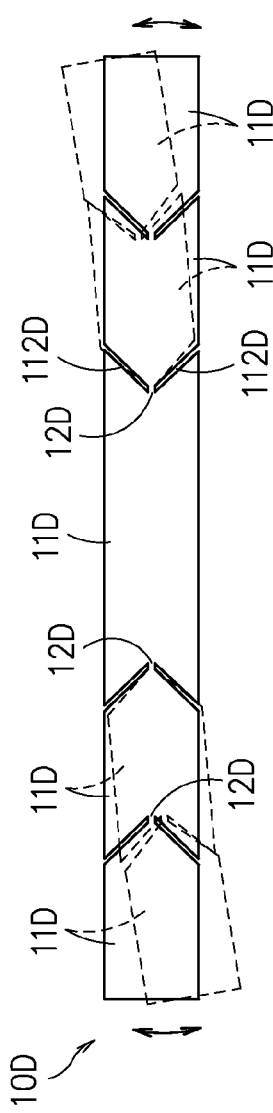

Basing upon the aforesaid bendable principle, the frame 10 can be formed with a variety of configurations. In the frame 10B shown in FIG. 7, the connector 12B used for connecting two neighboring unit cells 11B is sandwiched between the two unit cells 11B at a position about the centers of two, by that the frame 10B is enabled to be bended with respect to both of its top and bottom sides. In the frame 10C shown in FIG. 8, it is constructed similar to the frame 10 shown in FIG. 4 that the connector 12C used for connecting two neighboring unit cells 11C is sandwiched between the two neighboring unit cells 11C at a position about the bottoms of two. However, it is different those embodiments disclosed in FIG. 5 and FIG. 6 in that: each groove 112C formed by the enclosure of two neighboring sides of any two neighboring unit cells 11C is sloped with respect to the configuration plane by a specific angle; and the grooves 112C are symmetrically disposed on the configuration plane with respect to a center line of the frame 10C, i.e. the slopping of the grooves 112C arranged at the opposite side of the center line are reversed. It is noted that the grooves 112C can be sloped by the same angle or not. Please refer to FIG. 9, which is a variation of the frames shown in FIG. 7 and FIG. 8. In FIG. 9, the connector 12D used for connecting two neighboring unit cells 11D is sandwiched between the two unit cells 11D at a position about the centers of two, while allowing each groove 112D sandwiched between two neighboring sides of any two neighboring unit cells 11D to be formed as "⟨" or "⟩"; and similarly, the grooves 112D are symmetrically disposed on the configuration plane with respect to a center line of the frame 10D, i.e. the opening of the ⟨-shaped or ⟩-shaped grooves arranged at the opposite side of the center line are reversed. It is noted that all the ⟨-shaped or ⟩-shaped grooves can open to the same direction that is not limited thereby. Thus, the frame 10D can be bended with respect to both of its top and bottom sides.

Figure 12:
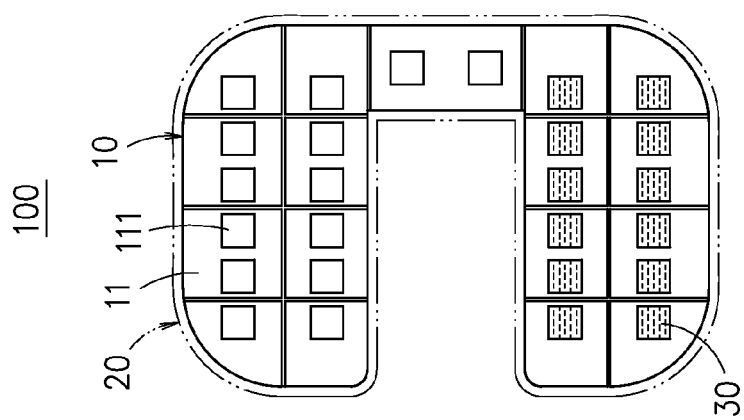
FIG. 10 to FIG. 12 are schematic diagrams showing the storage of liquid collected in the fluid collection apparatus of the invention is varying with the orientation of the apparatus.
Figure 11:
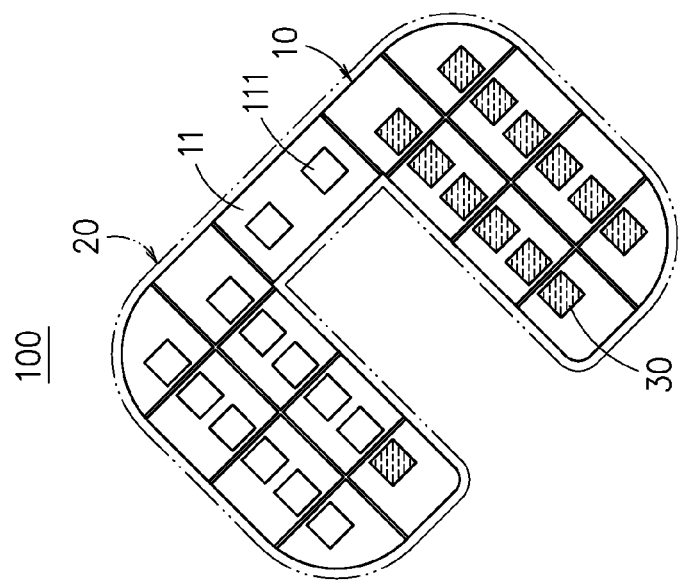
Figure 10:
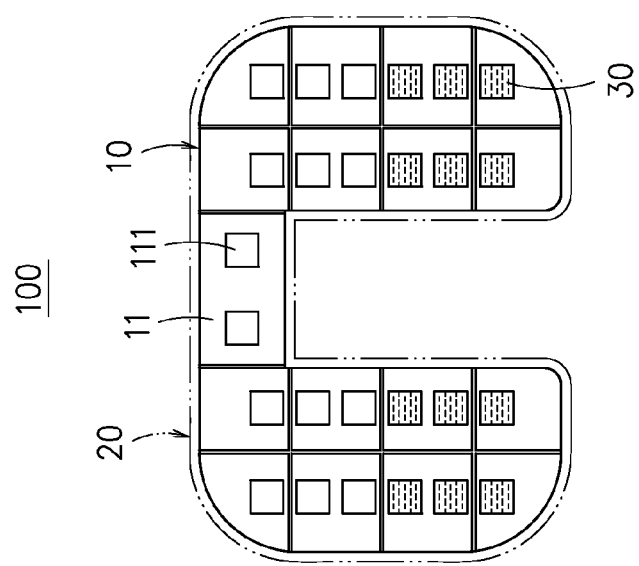

Please refer to FIG. 10 to FIG. 12, which are schematic diagrams showing the storage of liquid collected in the fluid collection apparatus of the invention is varying with the orientation of the apparatus. The reason why there are holes 111 formed on the frame 10 in the fluid collection apparatus 100 is that: the holes 111 are designed to act as fluid storage. It is noted that the volume of the fluid collection apparatus 100 will not change greatly since a fluid drained to the bag 20 will first be absorbed by the frame 10 and then will flood to the holes 111 as soon as the frame 10 is saturated whereas the bag 20 is rigidly supported by the frame 10. In addition, by counting the number of the holes 111 that are flooded, the amount of fluid being accumulated in the fluid collection apparatus 100 can be estimated and thus one can estimated the remaining fluid collection capability left in the fluid collection apparatus 100. Accordingly, the indication of the holes 111 in a unit cell being flooded by a fluid is that their corresponding unit cell is saturated. Therefore, it is possible to determine whether the fluid collection apparatus 100 should be changed by counting the amount of the holes 111 in the apparatus that are not flooded by fluid. As shown in FIG. 10, there are twelve holes 111 that are already flooded by a fluid 30 and there are fourteen left that are not flooded. Another characteristic of the fluid collection apparatus 100 is that: it is not a directional apparatus. As shown in FIG. 11 and FIG. 12 that the fluid collection apparatus 100 is slanted or even rotated by 90 degrees with respect to FIG. 10, there are still twelve holes 111 that are flooded by the fluid 30 and the number of holes being flooded will not change with the slanting or rotation of the fluid collection apparatus 100. Moreover, the shapes of the holes 111 are not limited by the rectangular shape shown in the aforesaid embodiments, they can be formed as a circular, a polygon or any geometrical shapes of any size, and can be arranged in any formation. However, it may have all the holes 111 on a fluid collection apparatus 100 to be formed of the same size and shape, and being arranged in an array.

Please refer to FIG. 13, which is a three-dimensional view of an apparatus for fluid collection according to another embodiment of the invention. The fluid collection apparatus 100E comprises: a frame 10E and a bag 20E, in which the frame 10E is received inside the bag 20E; and the bag 20E is connected to a conduit 21E and an exhaust tube 22E provided for any gases in the bag 20E to be exhausted out of the bag 20E therefrom. In addition, the bag 20E is configured with a window 23E, that is made of a waterproof, ventilative material, such as polytetrafluoroethylene (PTFE) or expanded polytetrafluoroethylene (ePTFE). During the draining of fluid into the bag 20E, it is inevitable that there are gases being introduced into the bag 20E as well, or in some situation, there are already gases existed inside the bag 20E. Therefore, for avoiding the volume of the fluid collection apparatus 100E from being propped up by the introduced gases, the gases are exhausted out of the bag 20E from the exhaust tube 22E and the window 23E. Moreover, the frame 10E is composed of a plurality of unit cells 11E as the plural unit cells 11E are interconnected by the use of connectors 12E. The plural unit cells 11E are coplanar-disposed on a configuration plane as an inverted U-shaped array with an indentation 113E, in that the indentation 113E is designed for a pump 40 to fit therein so as to prevent the pump 40 from extruding out of the fluid collection apparatus 100E. In another word, the indentation 113E is specifically designed to match with the size of the pump 40. Moreover, there are connecting devices, such as Velcro tapes, being arranged in the indentation 113E at positions where they are supposed to have contact with the pump 40, by that the pump 40 can be fixed inside the indentation 113E and thus integrated into the bag 20E. It is noted that if there is no requirement for arranging a pump 40 in a fluid collection apparatus 100E, the referring fluid collection apparatus 100E will not be configured with a frame 10E having an indentation 113E. As shown in FIG. 13, the conduit 21E is connected to the pump 40 while the pump 40 is further connected to a reservoir containing a liquid by another connecting tube 41; thereby, the liquid is withdrawn from the reservoir by the action of the pump 40 and then fed into the bag 20E through the conduit 21E where it is absorbed by the frame 10E.

Figure 14:
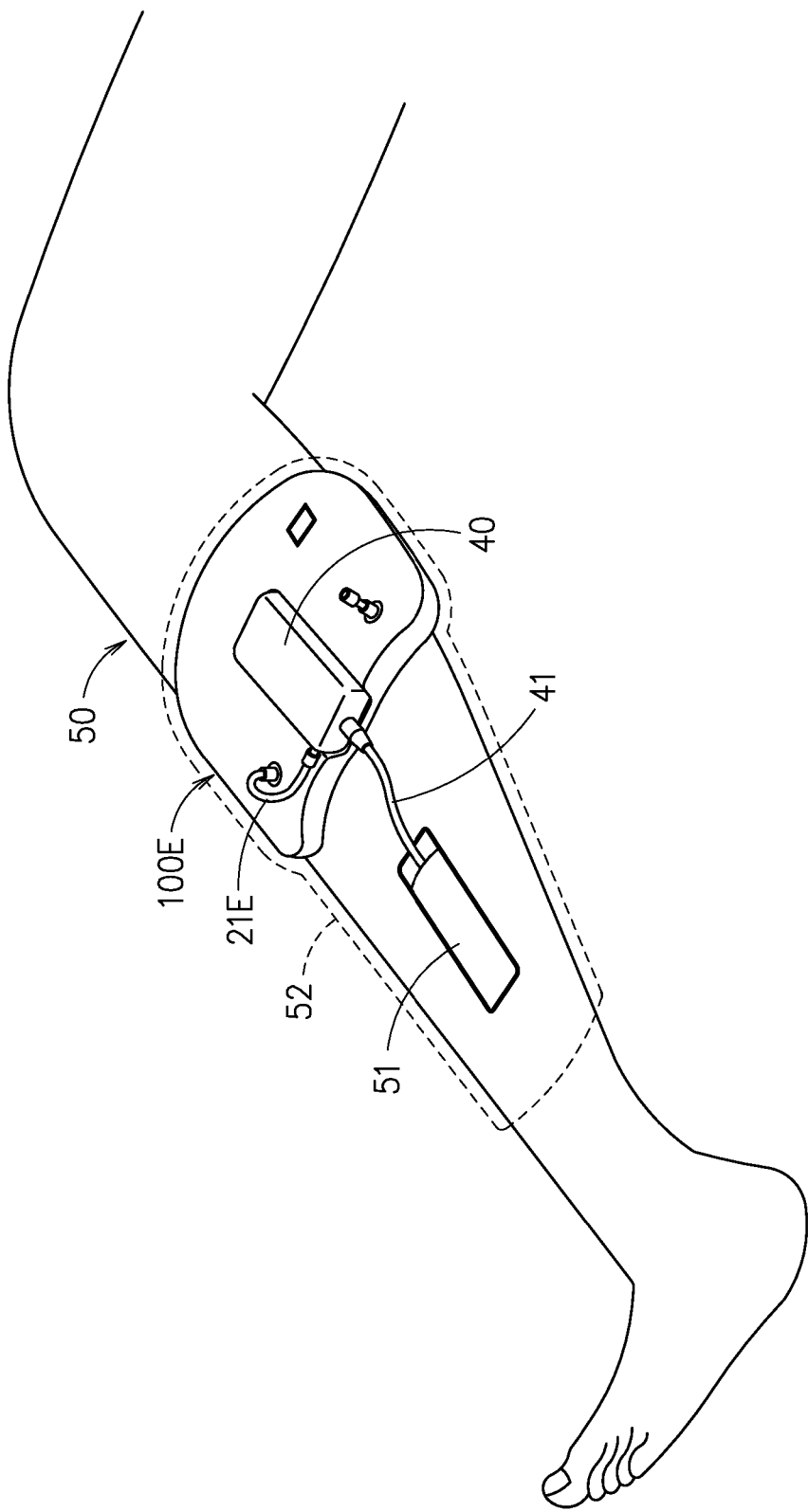
FIG. 14 is a schematic diagram showing the fluid collection apparatus of FIG. 13 is worn on a human lower leg.

Please refer to FIG. 14, which is a schematic diagram showing the fluid collection apparatus 100E of FIG. 13 is worn on a human lower leg 50. In FIG. 14, the connecting tube 41 is connected to a dressing 51 inside a wound on a lower leg 50 of a patient, and the fluid collection apparatus 100E is bound on the lower leg 50 by a fixing device 52 such as elastic bandage or gauze. As the fluid collection apparatus 100E is flexible, it can be bended complying with the curve of the low leg 50 to fit smoothly thereon. As soon as the pump 40 is activated, the tissue liquid absorbed by the dressing 51 is withdrawn through the connecting tube 41 to the pump 40, and then fed into the bag 20E through the conduit 21E where it is absorbed by the frame 10E. During the fluid collecting process, the amount of fluid already being accumulated in the fluid collection apparatus 100E can be monitored at all time, and thereby the remaining fluid collection capability left in the fluid collection apparatus 100E can be estimated.

Figure 15:
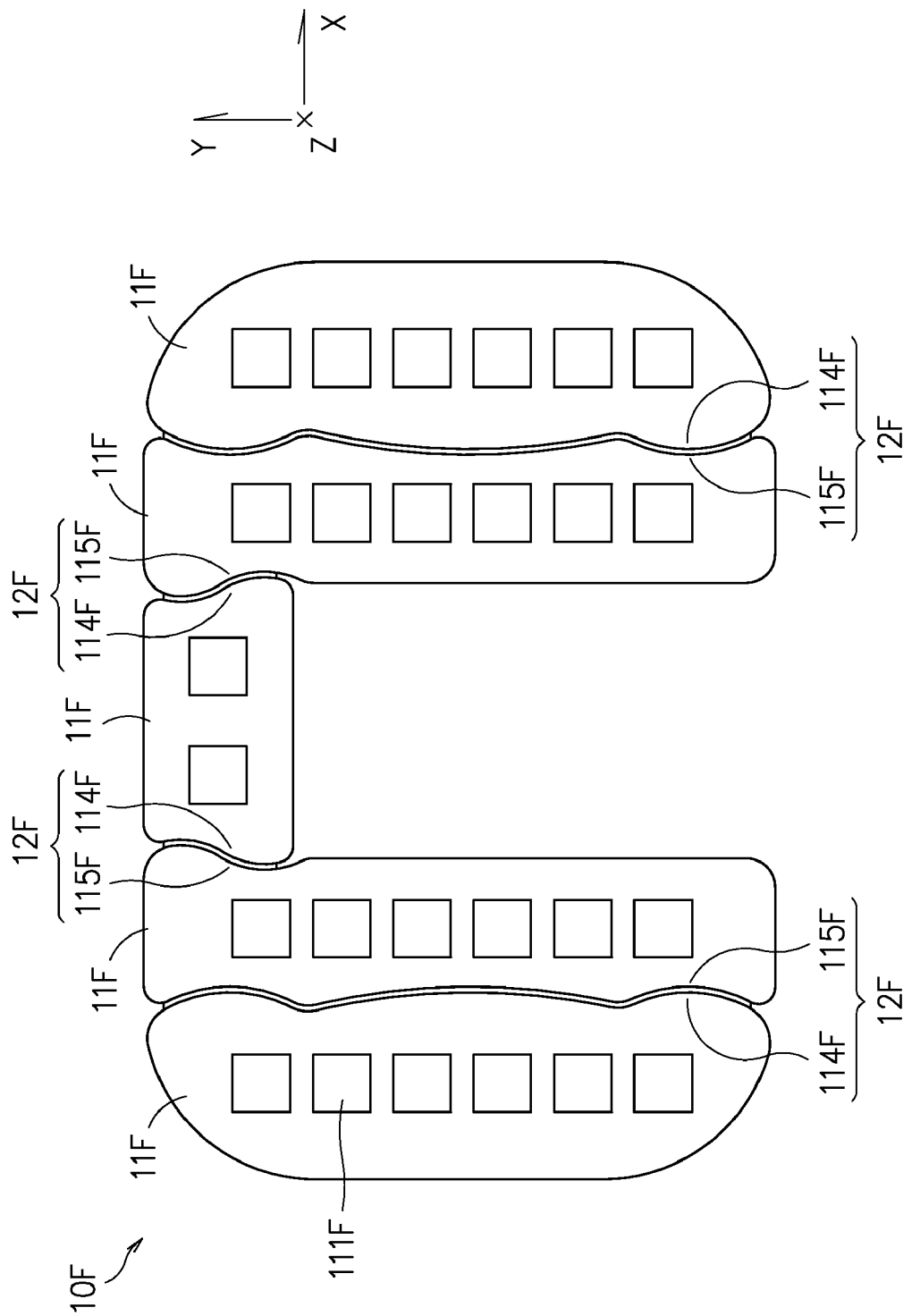
FIG. 15 is a front view of a frame used in another embodiment of the invention.

Please refer to FIG. 15, which is a front view of a frame used in another embodiment of the invention. In this embodiment, the frame 10E is compose of a plurality of unit cells 11F of the same thickness that are coplanar-disposed on a configuration plane along an X direction defined in a Cartesian coordinate system shown in FIG. 15 and each of the unit cell 11F is configured with a plurality of holes 111F. The present embodiment is characterized in that: the two neighboring sides of any two neighboring unit cells 11F are formed with irregular fringes 114F, 115F that can be mated with each other. As the irregular fringes 114F, 115F are acting as a connector 12F, any Y-directional slipping between the two neighboring unit cells 11F can be prevented. Similarly, when the plural unit cells 11F are arranged along the Y direction, the irregular fringes 114F, 115F acting as a connector 12F can prevent any X-directional slipping between the two neighboring unit cells 11F from happening.

Figure 16:
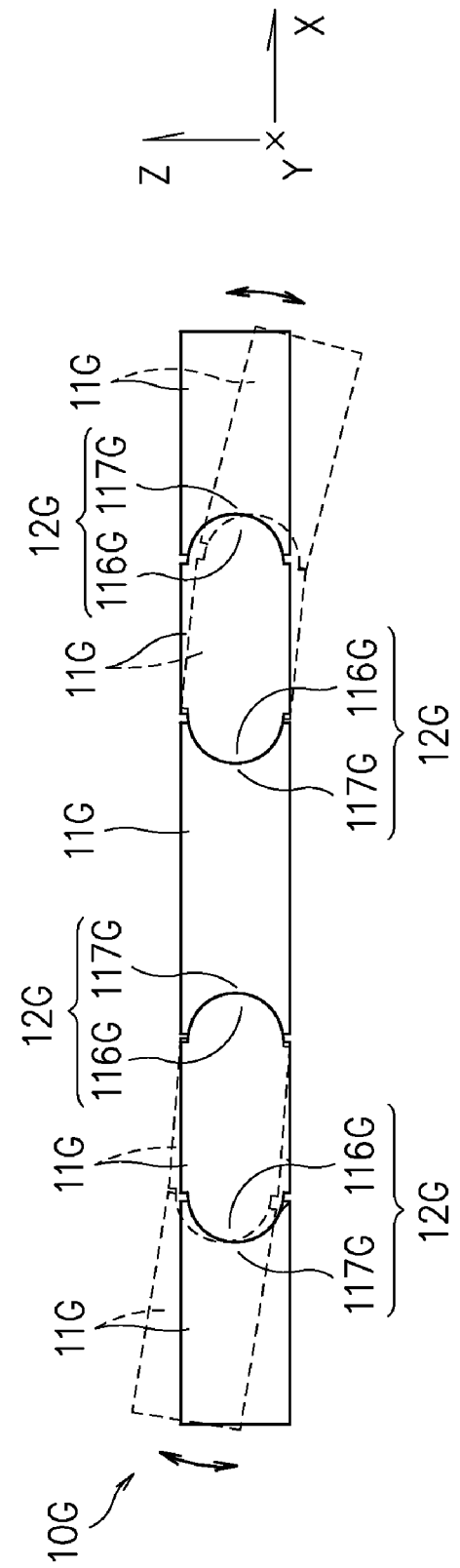
FIG. 16 is a bottom view of a frame used in another embodiment of the invention as it is being bended.

Please refer to FIG. 16, which is a Y-directional view of a frame 10G used in another embodiment of the invention as it is being bended. In this embodiment, the frame 10G is compose of a plurality of unit cells 11G along an X direction defined in a Cartesian coordinate system shown in FIG. 16 and each of the unit cell 11G is configured with a plurality of holes. Similarly, the plural unit cells 11G are connected by the use of connectors 12G. In this embodiment, each connector 12G, being a pivotal connecting mechanism formed on the two neighboring sides of any two neighboring unit cells 11G, includes a convex arc-shaped fringe 116G formed on one of the two neighboring sides and a concave arc-shaped fringe 117G formed on another side that are capable of mating with each for enabling the two neighboring unit cells 11G to joint pivotally and thus rotate. In addition, as the unit cells 11G are interconnected by pivotal connecting mechanism, any Z-directional slipping between the two neighboring unit cells 11G can be prevented.

To sum up, the fluid collection apparatus of the invention has the following advantages:

(1) The volume of the fluid collection apparatus will not change dramatically when it is used for fluid collection.
(2) The fluid collection apparatus of the invention can be wear or attached comfortably on a patient's limb or torso while allowing the patient to walk or exercise without too much trouble.
(3) The performance of the fluid collection apparatus of the invention will not be affected by how it is being worn on a patient, and the remaining fluid collection capability left in the fluid collection apparatus can be estimated by a simple measure.
(4) The fluid collection apparatus not only is a non-directional apparatus, but also is a device build with sufficient strength and space for resisting compression and storing fluid.
(5) The fluid collection apparatus is a light-weight device of leakage proof, smell-less and large storage capability.
(6) The fluid collection apparatus is a closed disposable device.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. An apparatus for fluid collection, comprising:
   a frame, composed of a plurality of coplanar-disposed unit cells, each being made of an absorbent polymer composite and formed with at least a penetrating hole for consequently enabling the frame to have a plurality of holes; and
   a bag, for receiving the frame while connected to a conduit provided for a fluid to flow in and out the bag therethrough;
   wherein the plural unit cells are coplanar-disposed on a configuration plane while enabling the two neighboring sides of any two neighboring unit cells to be formed with irregular fringes that can be mated with each other.

2. The apparatus of claim 1, wherein each unit cell is made of polyvinyl alcohol (PVA).

3. The apparatus of claim 1, wherein the plural unit cells are interconnected with each other by the use of at least a connector.

4. The apparatus of claim 3, wherein the plural unit cells are coplanar-disposed on a configuration plane and accordingly the at least one connector is disposed on the same configuration plane for enabling the sides of the plural unit cells corresponding to the at least one connector to be interconnected with each other while leaving the other sides thereof opposite to the at least one connector to be disconnected.

5. The apparatus of claim 3, wherein the plural unit cells are coplanar-disposed on a configuration plane and accordingly the at least one connector is disposed in a manner selected from the group consisting of: it is sandwiched between any two neighboring unit cells at a position about the centers of two; and it is sandwiched between any two neighboring unit cells at a position about the bottoms of two.

6. The apparatus of claim 3, wherein the unit cells and the connector are integrally formed.

7. The apparatus of claim 3, wherein the connector is made from an object selected from the group consisting of: an adhesive film and an adhesive tape.

8. The apparatus of claim 3, wherein each connector is a pivotal connecting mechanism.

9. The apparatus of claim 8, wherein each pivotal connecting mechanism, being formed on the two neighboring sides of any two neighboring unit cells, includes a convex arc-shaped fringe formed on one of the two neighboring sides and a concave arc-shaped fringe formed on another side that are capable of mating with each other for enabling the two neighboring unit cells to pivot thereby.

10. The apparatus of claim 1, wherein the plural holes of the frame are arranged as an array.

11. The apparatus of claim 1, wherein the plural holes of the frame are formed of the same shape.

12. The apparatus of claim 1, wherein each irregular fringe is a wave-shaped fringe.

13. The apparatus of claim 1, wherein the plural unit cells are arranged in an inverted U-shaped formation.

14. The apparatus of claim 1, wherein the bag is further connected to an exhaust tube provided for any gases in the bag to be exhausted therefrom.

15. The apparatus of claim 1, wherein the conduit is connected to a pump while the pump is further connected to a reservoir containing a liquid; thereby, the liquid is withdrawn from the reservoir by the action of the pump and then fed into the bag through the conduit where it is absorbed by the frame.

16. The apparatus of claim 1, wherein the bag is configured with a window made of a waterproof, ventilative material.

17. The apparatus of claim 1, wherein the bag is made of a waterproof, flexible material with a specific degree of transparency.

18. The apparatus of claim 17, wherein the bag is made of a polyvinyl chloride (PVC) film.

19. The apparatus of claim 1, wherein the plural unit cells are shaped different from one another.

20. An apparatus for fluid collection, comprising:
   a frame, composed of a plurality of coplanar-disposed unit cells, each being made of an absorbent polymer composite and formed with at least a penetrating hole for consequently enabling the frame to have a plurality of holes; and
   a bag, for receiving the frame while connected to a conduit provided for a fluid to flow in and out the bag therethrough;
   wherein the plural unit cells are interconnected with each other by the use of at least a pivotal connecting mechanism, and each pivotal connecting mechanism, being formed on the two neighboring sides of any two neighboring unit cells, includes a convex arc-shaped fringe formed on one of the two neighboring sides and a concave arc-shaped fringe formed on another side that are capable of mating with each other for enabling the two neighboring unit cells to pivot thereby.

21. An apparatus for fluid collection, comprising:
   a frame, composed of a plurality of coplanar-disposed unit cells, each being made of an absorbent polymer composite and formed with at least a penetrating hole for consequently enabling the frame to have a plurality of holes; and
   a bag, for receiving the frame while connected to a conduit provided for a fluid to flow in and out the bag therethrough;
   wherein the plural unit cells are arranged in an inverted U-shaped formation.

22. An apparatus for fluid collection, comprising:
   a frame, composed of a plurality of coplanar-disposed unit cells, each being made of an absorbent polymer composite and formed with at least a penetrating hole for consequently enabling the frame to have a plurality of holes; and
   a bag, for receiving the frame while connected to a conduit provided for a fluid to flow in and out the bag therethrough;
   wherein the plural unit cells are shaped different from one another.

* * * * *